US008637314B2

(12) United States Patent
Maurel

(10) Patent No.: US 8,637,314 B2
(45) Date of Patent: Jan. 28, 2014

(54) REVERSE MICELLES BASED ON PHYTOSTEROLS AND ACYLGLYCEROLS AND THERAPEUTIC USES THEREOF

(75) Inventor: Jean-Claude Maurel, Castries (FR)

(73) Assignee: Medesis Pharma SA, Baillargues (FR)

( * ) Notice: Subject to any disclaimer, the term of this patent is extended or adjusted under 35 U.S.C. 154(b) by 1201 days.

(21) Appl. No.: 11/718,513

(22) PCT Filed: Nov. 2, 2005

(86) PCT No.: PCT/IB2005/003592

§ 371 (c)(1),
(2), (4) Date: Nov. 11, 2008

(87) PCT Pub. No.: WO2006/048772

PCT Pub. Date: May 11, 2006

(65) Prior Publication Data

US 2009/0087406 A1    Apr. 2, 2009

(30) Foreign Application Priority Data

Nov. 2, 2004    (EP) .................................... 04025991

(51) Int. Cl.
    *C12N 15/88* (2006.01)
    *C12N 15/00* (2006.01)
    *A61K 9/127* (2006.01)
(52) U.S. Cl.
    USPC ............ 435/458; 514/938; 424/450; 435/455
(58) Field of Classification Search
    None
    See application file for complete search history.

(56) References Cited

U.S. PATENT DOCUMENTS 5,693,516 A * 12/1997 Blinkovsky ................... 435/188
6,129,924 A * 10/2000 Maurel et al. ................. 424/400

FOREIGN PATENT DOCUMENTS

| DE | 40 38 385 A1 | 4/1992 |
| EP | 0 366 277 A2 | 5/1990 |
| WO | WO91/14454 A1 | 10/1991 |
| WO | WO01/15201 A2 | 3/2001 |
| WO | WO03/030865 A1 | 4/2003 |

OTHER PUBLICATIONS http://en.wikipedia.org/wiki/Micelle, downloaded Oct. 9, 2011 (no author, issue, journal, or pages provided). 4 pages long.*
Venables, et al. (2001) Journal of Physical Chemistry, 105: 9132-38.*
International Search Report for PCT/IB2005/003592, Applicant: DEnderah Pharm PA.
Written Opinion for PCT/IB2005/003592, Applicant: Denderah Pharm PA.
"A Method for the Preparation of Submicron Particles of Sparingly Water-Soluble Drugs by Precipitation in Oil-in-Water Emulsions. II: Influence of the Emulsifier, the Solvent, and the Drug Substance," Sjöström*, B. et al., *Journal of Pharmaceutical Sciences*, vol. 82, No. 6, pp. 584-589, 1993, (XP000367863).

* cited by examiner

*Primary Examiner* — Robert M Kelly
(74) *Attorney, Agent, or Firm* — Saliwanchik, Lloyd & Eisenschenk

(57) ABSTRACT

The present invention relates generally to reverse-m ice liar system comprising a hydrosoluble therapeutically active agent. Reverse micelles according to the invention are particularly useful to deliver drugs. The present invention also relates to pharmaceutical composition comprising said reverse micelles and methods for preparing the same.

24 Claims, No Drawings

REVERSE MICELLES BASED ON PHYTOSTEROLS AND ACYLGLYCEROLS AND THERAPEUTIC USES THEREOF

CROSS-REFERENCE TO RELATED APPLICATIONS

This application claims priority to International Application No. PCT/IB2005/003592, filed on Nov. 2, 2005, which in turn claims priority to Application No. EP 04025991.1, filed on Nov. 2, 2004, the disclosures of which are herein incorporated by reference in their entirety.

FIELD OF INVENTION

The present invention relates generally to a reverse-micellar system comprising a hydrosoluble therapeutically active agent. Reverse micelles according to the invention are particularly useful to deliver drugs. The present invention also relates to the pharmaceutical composition comprising the said reverse micelles and methods for preparing the same.

BACKGROUND OF THE INVENTION

Over the last years, various approaches have been proposed to improve the delivery of drugs at the target site. Firstly, the drug must be administered by a suitable and easy route, such as via oral or rectal routes, and secondly the active ingredient must be delivered at the target cells in an active form. Some drugs, in particular proteins and peptides, are poorly absorbed and unstable during passage through the gastrointestinal tract (GIT). Many attempts have been made so far to improve delivery, in particular via the oral route, of polypeptides and peptides, such as for instance insulin (for treating diabetes), interferons (for treating hepatitis), cytokines (for treating cancers), etc. However, today the administration of these drugs is via parenteral injection. Today, 40% of the new drugs can only be administered through parenteral injection.

Despite the inherent problems faced when attempting to administer proteins and peptides orally, various approaches have been proposed to improve oral absorption. Plausible strategies have included chemical modification to stabilise the drug and/or to render it more lipid-soluble and hence improve its chances to diffuse across the lipid membrane or the GIT. Other researchers have added stabilising agents such as peptidase inhibitors (e.g. aprotinin) to reduce metabolic loss, while others have used various absorption promoting agents in the form of non-ionic surface active agents, bile salts and analogues thereof, phospholipids, chelating agents or acyl carnitine. Numerous patents and publications describe also methods for encapsulating active ingredients into nano- or micro-particles. But, so far, none of the developed delivery systems is totally satisfactory, particularly for insulin. For instance, the delivery systems disclosed so far have permitted an insulin absorption of 2-5% only.

Subjects suffering from diabetes type 1 or 2 are often treated with insulin. While the injection devices are improving and are less invasive (e.g. pen-like devices), injections still present disadvantages and remain very unpopular. Non-injectable formulations will present great advantages. In addition to being more patient-friendly, such formulations could improve compliance, leading to better treatment and a reduction in diabetes-related complications.

The inventors have previously uncovered that stirring two types of lipids with some metallic salts allowed to increase metal bioavailability and consequently to obtain same therapeutic activity with 1000 to 5000 lower doses; the potential toxicity of the said metal salts could then be reduced [see U.S. Pat. No. 6,129,924, WO 02/36134 and WO 2004/075990, for examples].

It is an object of the present invention to overcome disadvantages of the prior art. More particularly, it is an object of the invention to provide a drug delivery system comprising an active ingredient, which can be administered orally and give a satisfactory drug bioavailability.

SUMMARY OF THE INVENTION

The present invention relates to a transmembrane transport delivery system for the release of a therapeutic agent of interest, as well as the compositions and methods for preparing the delivery system. More particularly, the present invention provides a reverse-micellar transport system for dispensing an agent of interest. More specifically, reverse micelles according to the invention promote the absorption of biologically active molecules across mucosal epithelial barriers and allow the active ingredients to be internalised by target cells. The reverse micelles of the invention comprise more specifically at least one hydrosoluble therapeutically active ingredient, phytosterol, acylglycerol and water.

The present invention relates more particularly to reverse micelles with an aqueous core of less or equal to 100 nm.

The reverse micelles can be prepared according to a particular method using phytosterols and acylglycerols.

The said micelles are more particularly obtainable by the following method:
  (a) Contacting (i) phytosterol, (ii) acylglycerol, preferably diacylglycerol of fatty acids, (iii) water, in particular purified water, and (iv) at least one hydrosoluble therapeutic active ingredient,
  (b) Stirring mixture obtained in step (a), at 40° C. or less, and for a time sufficient to obtain formation of reverse micelles, said stirring is carried out mechanically at a speed from about 1000 to about 5000 r/min or by sonication.

The present invention further relates to a composition comprising reverse micelles of the invention and a pharmaceutically acceptable carrier, excipient or support.

DETAILED DESCRIPTION OF THE INVENTION

The following description is of preferred embodiments by way of examples only and without limitation to the combination of features necessary for carrying the invention into effect.

Reverse Micelles

The reverse micellar system according to the invention is characterized as a microemulsion comprising a dispersion of water-microdroplets in oil. The dispersion is stabilised by a surfactant (acylglycerol, more preferably diglycerol of fatty acids) at the water/oil interface. The reverse micellar phase can be defined as a system wherein water forms the internal phase and the hydrophobic tails of the lipids form the continuous phase. Reverse micelles containing oil(s), surfactant(s) and an aqueous phase are also characterized as water-in-oil microemulsions.

The size of micelles appears to vary in a linear way with the (water)/(surfactant) weight ratio W (solubilized water in the mixture/the surfactant in the mixture). As mentioned above, the relative weight quantity of water in the mixture (W) is preferably lower or equal to 2.5 and preferably lower or equal to 1 of the quantity of acylglycerol, preferably of diglyceride of fatty acids. W is more specifically 0.01 to 0.2. According to a particular embodiment, the ratio W is preferably from 0.05 to 0.18.

The reverse micelles, such as size of the core thereof, can be characterized by various methods:
X-Ray Scattering
Neutrons Scattering
Transmission Electron Microscopy (TEM)
Dynamic Light Scattering (DLS)

The ratios of the lipidic constituents (phytosterols and acylglycerol) in the reverse-micellar system according to the invention can vary in a large extent, for instance the weight ratio phytosterol/acylglycerol can range from 0.01 to 1 (inclusive). According to a particular embodiment, an excess of acylglycerol (preferably diglyceride of fatty acids) can be used as compared to phytosterol (preferably sitosterol). More particularly, the weight ratio phytosterol/acylglycerol is more than or equal to 0.1, more preferably from 0.1 to 0.2.

The compounds of the reverse-micellar system can be analysed by appropriate means. More specifically, phytosterol can be identified by gas chromatographic analysis and acylglycerol by high-performance liquid chromatography (HPLC), in particular with a light scattering detector, on a silica column (kromasil C18), in the presence of an eluent, e.g. isocratic acetonitrile. Gas chromatography can also be used to analyse diacylglycerides.

Reverse micelles are dynamic systems. Brownian motion causes perpetual collisions of micelles, which lead to coalescence of micelles and exchange of the aqueous cores. Separation and regeneration of micelles occur and allow chemical reactions between different solutions. The exchange rate between micelles increases in particular with temperature, the length of hydrocarbon chains of the surfactant, and W ratio (free water increases the said exchange). Within the context of the invention, and contrary to what is expected in nanotechnology, aqueous core of micelles must have a specific size allowing one or more molecules of the therapeutically active ingredient, introduced when preparing the micelles, to be stabilised therein. Size of the aqueous core is preferably less or equal to about 100 nm and preferably more or equal to 5 nm. Ratio W as defined above is preferably less or equal to about 2.5.

Analysis by X-ray scattering of the product as described in example 1 revealed reverse micelles in a micro emulsion.

The major advantage of the present invention over the prior art is the use of phytosterol, more preferably sitosterol, for the preparation of reverse micelles. Accordingly, the invention provides an absorption of the compounds to be delivered across mucosa, preferably across mouth and rectal mucosa, more preferably across mouth mucosa. Also, reverse micelles of the present invention provides an important bioavailability with low variability of absorption. Another beneficial aspect of the reverse micelles of the present invention is that they can be prepared with varying sizes in order to adapt them to the active ingredients to be included therein.

Method for Preparing Reverse Micelles

In a particular embodiment, the invention relates to a method for preparing reverse micelles presenting an aqueous core of less or equal to 100 nm and comprises at least one hydrosoluble therapeutic active ingredient, phytosterol, acylglyceride and water, wherein said method comprises the following steps:
  (a) Contacting (i) phytosterol, (ii) acylglycerol, preferably diacylglycerol of fatty acids, (iii) water, in particular purified water, and (iv) at least one hydrosoluble therapeutic active ingredient, wherein the ratio W=[water]/[acylglycerol] is preferably less or equal to about 2.5,
  (b) Stirring mixture obtained in step (a), at 40° C. or less, and for a time sufficient to obtain formation of reverse micelles, said stirring is carried out mechanically at a speed from about 1000 to about 5000 r/min or by sonication.

The obtained and recovered reverse micelles are then particularly useful as a drug delivery system. Step (b) of the process is of particular importance since it allows to obtain reverse micelles, which are then useful as a transport system for delivering drug at the target site.

The used compounds in step (a) will be described in more details below.

Stirring of the mixture obtained by step (a) is more particularly carried out at a temperature less than or equal to 40° C., preferably ranging from 30° C. to 38° C., more preferably from 30° C. to 35° C., for a time sufficient to obtain formation of reverse micelles. The time sufficient can vary in particular upon the used stirring techniques, i.e., mechanical stirring or sonication. The time of mechanical stirring or sonication is anyhow the time needed to convert the initial mixture into a monophasic reversed micellar solution.

In a particular embodiment, the therapeutically active ingredient is first solubilised in water (preferably purified water), which is then put into contact with the other constituents (step(a)).

One skilled in the art knows how to select excipients or components to be used along with the composition according to the present invention in order to keep their beneficial properties. In particular, the presence of glycerol can, when introduced in large amount, prevent the formation of reverse micelles or break the reverse micellar system. More specifically, no more than 1%, and preferably no, glycerol (percent expressed by weight of glycerol/total amount of water of the composition) is used for the preparation of the reverse micelles of the present invention.

Sonication

Ultrasounds of sonication lead to an acoustic cavitation within liquids, i.e., bubble formation in the liquid. Ultrasound produces an homogeneous stirring within all parts of the reaction chamber and provides little turbulence within the liquid. It is the most reliable and useful method to prepare nanoparticles. Stability of the obtained microemulsions is due in particular to acylglycerol (preferably diglyceride of fatty acids) acting as a surfactant.

Different types of sonication materials can be used at the laboratory or industrial scales. High-intensity ultrasound process is the most suitable process. To prepare small quantities, materials of 400 W or 600 W with ultrasounds at 20 kHz give satisfactory results and are thus preferred. Electronic control of temperature and emission duration of the process is also possible with that type of devices. Materials of the same type exist for industrial uses.

Physical parameters, in particular time (3-5 minutes, in one or more times), are dependent on the used material, volumes of the mixture and viscosity thereof. One skilled in the art can readily define such parameters. More specifically, temperature of the mixture must not exceed 40° C. as to avoid degradation of the reactants. Temperature is preferably lower than about 38° C., even more preferably lower than about 35° C.

Mechanical Stirring

The usual materials use propellers whose fast movements generate turbulences and swirls allowing the interpenetration of particles, and the formation of nanoparticles within the mixture.

Stirring speed is preferably ranging from 1 000 to 5 000 r/minute. The implemented volumes, device, stirring speed and W ratio depend on and must be adapted with the therapeutically active ingredient.

As described above, temperature of the mixture must not exceed 40° C. as to avoid degradation of the reactants. Temperature is preferably lower than about 38° C., even more preferably lower than about 35° C.

Reverse Micelles Compounds
Acylglycerol

Acylglycerides, more particularly acylglycerides of fatty acids, useful for the preparation of the reverse-micellar system according to the invention can be isolated from the majority of animals and more preferably plants.

Acylglycerols include mono-, di- or triacylglycerols. In a particular embodiment, mono-, di- or triglycerides preferentially used in the present invention present the following formula (I):

in which:
- $R_1$ is an acyl residue of a linear or branched, saturated or unsaturated fatty acid having between 14 and 24 carbon atoms, an hydrogen atom, or a mono-, di- or tri-galactose or glucose;
- $R_2$ is an acyl residue of a linear or branched, saturated or unsaturated fatty acid having between 2 and 18 carbon atoms;
- $R_3$ is an acyl residue of a linear or branched, saturated or unsaturated fatty acid having between 14 and 24 carbon atoms, or an hydrogen atom.

According to a preferred embodiment, at least one of $R_1$ and $R_3$, preferably only one, represents an acyl residue of oleic acid (C18: 1[cis]-9).

According to a particular aspect, $R_2$ has one unsaturated bond (e.g; ethylenic bond) and has advantageously 18 carbon atoms, preferably $R_2$ is an oleic acid residue (oleoyl group), one of its positional isomers with respect to the double bond (cis-6,7,9,11 and 13) or one of its iso-branched isomers.

According to another particular aspect, $R_1$ represents an oleoyl group.

According to another particular aspect, $R_2$ represents an acetyl group.

According to a preferred embodiment, $R_3$ represents an hydrogen atom.

Unsaturated vegetable oils are particularly advantageously used as source of acylglycerols, especially olive oil from the first cold pressing.

As a general rule, an oil containing a high concentration of oleic acid will be chosen as a useful source of acylglycerols according to the invention. Such an oil usually contains a high proportion of acylglycerols useful according to the invention.

According to a particular aspect of the invention, the preferred diglycerides of fatty acids are selected in the group consisting of 1,2-diolein and 1-oleoyl-2-acetyl glycerol.

A certain number of them, and more particularly those which are found to be the most active in the applications sought after, also exist commercially. This is the case particularly for 1-oleoyl-2-acetylglycerol and 1,2-dioleoylglycerol, which exist as commercial products with a high purity content. In particular, glyceride monooleate containing about 44% of dioleic glycerides, from which about 14% is 1,2-diolein. Such a compound is pharmaceutically accepted (*European Pharmacopeia* (4$^{th}$ Edition), USP 25/NF20, and Japanese Standard of food Additives). Such product is for instance commercially available by Gattefossé Company under the name PECEOL®.

Phytosterols

The sterols useful for the preparation of the reverse-micellar system according to the invention are phytosterols (vegetable sterols). Sitosterol is the preferred phytosterol useful for the reverse-micellar system according to the invention. Phytosterol has many advantages over cholesterol, phytosterol being able to cross mucosa, in particular mouth and rectal mucosa. Consequently, reverse micelles of the present invention provide a mean to bypass the inconvenient or unpleasant parenteral route and, at the same time, prevent the material to be administered through the stomach, which is a hostile environment for many materials, including proteins. Accordingly, as a delivery mean, reverse micelles of the present invention are very advantageous in that they allow an important and homogenous absorption of the active ingredient to be administered.

The sitosterol incorporated in the reverse-micellar system of the invention can be [beta]- or [gamma]-sitosterol, preferably [beta]-sitosterol, or can be introduced in the form of a plant extract containing at least one of these two forms of sitosterol.

It is in particular possible to use various commercial products. More particularly, commercial sitosterol which is extracted from soya can be used. In such a product, the sitosterol generally represents from 50 to 70% by weight of the product and is generally found in a mixture with campesterol and sitostanol in respective proportions in the order of 15% each. Commercial sitosterol which is extracted from a variety of pine called tall oil can also be used. In general, it will be possible to use the sitosterol in a mixture with sitostanol. Preferably, said mixture comprises at least 50% sitosterol by weight of the mixture.

One will be able to obtain beta-sitosterol having a purity higher than 95%, or even 99%, while proceeding in the following way: one carries out several successive recrystallizations with acetone of commercial mixture, which allows a pre-purification of beta-sitosterol by elimination of the campestanol and of the sitostanol present in the mixture. Then, one subjects the product thus prepurified to 1 to 3 steps of purification by high pressure liquid chromatography on a preparative column C18 by using eluant mixtures, such as methanol, in particular methanol 100% or mixtures of methanol and acetonitrile, in particular of mixtures 80-20 or any intermediate mixture making it possible to obtain sitosterol with a purity higher than 95 or even 99%. This purity is determined by gas chromatography.

Sitosterol and thus sitostanol can also be prepared by extraction from plants according to the techniques in the literature, for example p. 95 of the thesis presented at Montpellier by Claude Cerdon entitled <<Modulation de la production de sapogenines steroidiques en reponse a l'inhibition de la synthese de sterols>>.

This extraction is carried out advantageously by complexation with metals, according to the method described in particular in French patent FR 2 316 247 in which is described a method for isolating 3-hydroxy-steroids and 3-oxo-steroids from a mixture containing these compounds.

To effect this extraction any plant or product of plant origin known for its relatively high content of sitosterol can be used.

By way of examples of plants or products of plant origin with a relatively high free sitosterol content may be mentioned in particular olive oil, soya bean oil cotton leaves, coffee leaves, wheatgerm, for which the free phytosterol content and the percentage of sitosterol in the free phytosterol fraction are given in the table below:

| SPECIES | content/kg | % of phytosterol fraction |
|---|---|---|
| olive oil | 1310 mg | 91% |
| soya oil | 1908 mg | 53% |
| cotton leaves | 3961 mg | 93% |
| coffee leaves | 9914 mg | 51% |
| wheatgerm | 17336 mg | 67% |

% is expressed by weight.

The relative content of sitostanol has not been studied. It must also be pointed out that the free phytosterol fraction contains a proportion of the 24 R and 24 S isomers, which are variable according to the plant. This proportion is not well known, since it has been little studied, if at all.

This proportion as well as the relative quantity of sitostanol, which cannot be separated from the sitosterol during purification, could explain the better relative activity of the phytosterol fraction of some plants, and especially the excess of sitosterol necessary for the preparation of the reverse-micellar system described in the invention.

As mentioned above, the ratios of phytosterol and acylglycerol can vary in a large extent, for instance the weight ratio phytosterol/acylglycerol can range from 0.01 to 1 (inclusive). According to a particular embodiment, an excess of acylglycerol (preferably diglyceride of fatty acids) can be used as compared to phytosterol (preferably sitosterol). More particularly the weight ratio phytosterol/acylglycerol is more than or equal to 0.1, more preferably from 0.1 to 0.2.

Therapeutic Active Compound

Any hydrosoluble therapeutic agent can be used in the present invention. It includes, but is not limited to, polypeptides, proteins, polysaccharides, nucleic acids [DNA or RNA (more particularly RNAi) or fragments thereof] and aqueous pharmaceutical compositions.

Proteins with a particular therapeutic interest are more preferably used in the present invention. Since such active ingredients are unstable in biological medium, in particular they can be degraded by the endogenous enzymes present in the GIT, they are usually administered by an injectable route.

Agents of interest according to the invention are any therapeutic protein or glycoprotein, such as insulin, erythropoietin, leptin, growth factors, growth hormone releasing hormones, colony stimulating factors, hydrosoluble hormones (parathyroid hormone or fractions or analogues thereof, luteinising hormone releasing hormone (LHRH) or analogues thereof (e.g. nafarelin, buserelin, goserelin), polysaccharides (such as heparin), interferons, heparin-like compounds, and cytokines. It includes also DNA, RNA fragments or plasmids, RNA interference, immunogenic and/or vaccine agents, etc.

Such agent incorporated in the reverse-micellar system according to the invention can cross mucosal epithelial barriers and present thereby its therapeutic effect at the target site.

The hydrosoluble active ingredient is more preferably present in the aqueous core of the reverse micelles.

Stability and activity of the therapeutic agent can be controlled essentially by water concentration in the mixture. Studies have been carried out with enzymes dissolved in the aqueous phase and show that enzyme activity can be optimized and kinetics reaction depend on the relative concentration of water.

The amount of the active ingredients incorporated into the reverse micelle system is determined by their solubility in the hydrophilic phase (aqueous core). Preferably, the amount of therapeutic agent included in the reverse micelle system is dependent of the active ingredient.

Use of the Reverse-Micellar System

The reverse micelles of the invention improve bioavailability of the active ingredient included therein, allowing its therapeutic use at the target site with a reduced toxicity. Due to its microemulsion nature, the reverse-micellar system allows to provide different types of formulations, comprising excipients, vehicles or various supports, which can be administered by various routes, including mucosally, such as by mouth or rectal administration.

It is known today that a reverse-micellar system can be used for the preparation of nanomaterials, which act as microreactors. They can host proteins like enzymes. Catalytic reactions with water insoluble substrates can occur at the large internal water-oil interface inside the microemulsion. The activity and stability of biomolecules can be controlled, mainly by the concentration of water in this media.

Incorporation in a reverse-micellar system of therapeutic agents provides the following advantages: said agents are more stable, they can be absorbed via mucosa, transport of the micelles in the blood medium is not altered and an optimal biological effect of the active ingredients at the target site is obtained.

An object of the invention concerns a pharmaceutical composition comprising reverse micelles as defined above and a pharmaceutically acceptable carrier, excipient or support.

A further object of the invention concerns the use of reverse micelles as defined above for preparing a pharmaceutical composition intended for the delivery, more specifically the mucosal delivery, of one or more hydrosoluble therapeutic active agents. The pharmaceutical composition is more particularly intended to prevent or treat one or more symptoms associated with a disease or disorder.

Another object of the invention concerns methods for the delivery of one or more hydrosoluble therapeutic active agents to a mammal (in particular human), said methods comprising administering the said reverse micelle composition as defined above. In a specific embodiment, the present invention provides methods for the mucosal delivery of one or more hydrosoluble therapeutic active agents, said methods comprising mucosally administering to said mammal (in particular human) a reverse micelle composition as defined above. The present invention provides methods for the prevention, treatment, or amelioration of one or more symptoms associated with a disease or disorder in human, said methods comprising administering to said human in need thereof an effective amount of a reverse micelle composition as defined above and comprising one or more hydrosoluble therapeutic agents useful in the prevention, treatment or amelioration of one or more symptoms associated with said disease or disorder. In a specific embodiment, the present invention provides methods for the prevention, treatment or amelioration of one or more symptoms associated with a disease or disorder, said methods comprising mucosally administering to a subject in need thereof an effective amount of a reverse micelle composition as defined above and comprising one or more hydrosoluble therapeutic agents useful in the prevention, treatment or amelioration of one or more symptoms associated with said disease or disorder.

In particular, the hydrosoluble therapeutic active agent is as defined above, including a protein, polypeptide, peptide, glycoprotein, polysaccharide, a nucleic acid as identified above, or mixtures thereof.

Where polypeptides and peptides are for instance insulin, interferons, and cytokines, the treated diseases are more specifically diabetes, hepatitis, and cancers, respectively.

Where immunogenic and/or vaccine agents are used, the reverse micellar system of the invention obtained therefrom may be used as a vaccine.

As a pharmaceutically acceptable excipient, vehicle or carrier, any excipient vehicle or carrier well-known to the person skilled in the art may be used. The following can be cited as examples in a non-limiting way: lactose, corn starch, glucose, sucrose, sweetening agents such as malitol syrup, gum arabic, gelatine, carrhagenans, stearic acid, magnesium stearate, dextrin, maltodextrins, mannitol, talc, fats from natural origin, particularly oils of vegetable origin rich in unsaturated fatty acids and phytosterols. In particular, if eventually necessary, other additives well-known to the person skilled in the art such as stabilisers, drying agents, binders or pH buffers may be used. Preferred excipients in accordance with the invention promote adherence of the finished product to the mucosa.

The compositions of the invention can be administered in different ways, in particular via the oral route, with a buccal or digestive absorption, or more generally via mucosal tissue in mouth.

As used herein, the terms "mucosa" and "mucosal" refer to a mucous tissue such as epithelium, lamina propria, and a layer of smooth muscle in the digestive tract. "Mucosal delivery", "mucosal administration" and analogous terms as used herein refer to the administration of a composition to the mucosal tissue. "Mucosal delivery", "mucosal administration" and analogous terms include, but are not limited to, the delivery of a composition through bronchi, gingival, lingual, nasal, oral, vaginal, rectal, and intestinal mucosal tissue.

In a preferred embodiment of the invention, the reverse micelle compositions of the invention are mucosally administered as a capsule, caplet, aerosol, spray, solution, suspension, emulsion, cachet, tablet, soft elastic gelatin capsule, aerosol, powder or granule. The compositions of the invention can be introduced in liquid form into capsules which releases their contents in the mouth. Preferably, the reverse micelle compositions of the invention are administered to a mammal, more preferably a human to prevent or treat a disease or disorder.

The following examples are intended to exemplify the operation of the present invention but not to limit its scope.

EXAMPLES

Example 1

Preparation of a Transport Delivery System for Administering Insulin by a Rectal Route into an Animal To 1 g of sitosterol solubilised in 2 ml of ethanol, 1 ml of purified water comprising 100 UI insulin (Umuline Zn long acting) then 40 ml of Peceol® (glyceride monooleate commercially available by Gattefossé) are added. Sonication of the mixture is carried out in two times (3 minutes each), by monitoring the temperature at less than 35° C.

The obtained product is constituted of a homogeneous mixture of stable reverse nano-micelles containing insulin.

It can then be administered into an animal at 2 ml/kg by the rectal route (5 UI insulin Zn/24 h/kg).

Example 2

Preparation of a Transport Delivery System for Oral Administration of Insulin into a Subject To 10 g of sitosterol solubilised in 10 ml of ethanol, 2 ml of purified water containing 200 UI d'insulin (Umuline long acting) then 28 ml of Peceol® are added.

Sonication of the mixture is carried out in two times (3 minutes each), by monitoring the temperature at less than 35° C.

The obtained product is constituted of a homogeneous mixture of stable reverse nano-micelles containing insulin. It is introduced into capsules, each containing 1 g of the obtained product (5 UI of fast acting insulin per capsule). It can then be administered to a person in need of insulin. Said person breaks the capsule in his mouth and keeps the liquid obtained therefrom in his mouth for about one minute (so that sitosterol in the mixture adheres to the mucosa of the mouth and allows a fast absorption).

Example 3

Preparation of a Transport Delivery System for Oral Administration of Erythropoietin into a Subject 10 g of sitosterol solubilised in 10 ml of ethanol, 2 ml of an aqueous solution containing 80 000 UI of erythropoietin (EPREX 40 000 UI/ml), then 28 ml of Peceol® are mixed.

The mixture is stirred with a hotplate stirrer at 1200 r/minute, by monitoring the temperature at less than 35° C.

The obtained product is constituted of a homogeneous mixture of stable reverse nano-micelles containing erythropoietin. It is introduced into capsules, each containing 1 g of the obtained product (1000 UI erythropoietin per capsule). It can then be administered to a person in need of erythropoietin. Said person breaks the capsule in his mouth and keeps the liquid obtained therefrom in his mouth for about one minute (so that sitosterol in the mixture adheres to mucosa of the mouth and allows a fast absorption).

Example 4

Preparation of Reverse Micelles Containing Erythropoietin

To 3 g of sitosterol solubilized in 4.5 ml of ethanol, 1 ml of EPREX® containing 2000 UI EPO, and 72 ml of Peceol® are added.

The mixture is stirred with a magnetic stirrer heating at 35° C. for 15 minutes.

The W ratio is 0.04.

It can then be administered into rats at 2 ml/kg by the rectal route (50 UI/kg).

Example 5

Preparation of Reverse Micelles Containing Erythropoietin

To 3 g of sitosterol solubilized in 4.5 ml of ethanol, 2 ml of EPREX® containing 4000 UI EPO, and 72 ml of Peceol® are added.

The mixture is stirred with a magnetic stirrer heating at 35° C. for 15 minutes.

The W ratio is 0.08.

It can then be administered into rats at 2 ml/kg by the rectal route (100 UI//kg).

Example 6

Preparation of a Transport Delivery System for Intra Rectal Administration of Reverse Micelles Containing Plasmid and Administration 125 μg of sitosterol solubilised in 200 μl of ethanol, 250 μl of an aqueous solution containing 3 mg of plasmid pEGFP-N1, then 4.75 ml of Peceol® are mixed.

The mixture is stirred with a hotplate stirrer at 1200 r/minute, by monitoring the temperature at less than 35° C.

The obtained product is an homogeneous mixture of stable reverse nano-micelles containing plasmid.

Administered Products

The pEGFP-N1-containing reverse micelles are prepared as described above. pEGFP-N1 (purchased from Clontech), the mammalian expression vector for enhanced green fluorescent protein (eGFP), is used after transformation into competent *Escherichia coli* Top10 cells (Invitrogen) and purification using a EndoFree Plasmid Mega Kit from Qiagen Ltd according to the manufacturer's instructions.

Methods

Eight rats (Wistar, 250-300 g) are injected by a rectal route with 500 μl of the product.

Blood samples are collected at 1, 2, 4 and 8 minutes after injection (2 rats per time) in anti-coagulant-containing tubes. After a centrifugation at 1500 rpm for 25 min, the plasma is used for transfection studies.

HepG2 (human hepatoma cell line) and CV1 (monkey kidney fibroblast cell line) are maintained in Dulbecco's modified Eagle's medium supplemented with 10% foetal calf serum (Invitrogen, Carlsbad, Calif.) and seeded at a density of $5 \times 10^4$ cells/well in 24-well plates 24 hours before transfection studies.

For the transfection, the culture medium is removed and 200 μl of rat plasma containing the reverse micelles containing the plasmid pEGFP-N1 are added to the different dishes for 20 minutes at room temperature. After addition of 500 μl of fresh medium, cells are cultured for 48 h prior to measuring gene expression under a fluorescence microscope by determination of the percentage of fluorescent cells.

Negative control plasma corresponds to sample of rat non-injected with the reverse micelles containing plasmid pEGFP-N1. FuGENE™6 (Roche) is used, as instructed by the manufacturer, as positive control of transfection.

Results

| Cell line | 1' | 2' | 4' | 8' | FuGENE ™ |
|---|---|---|---|---|---|
| % of transfection obtained (% of fluorescent cells) | | | | | |
| Human hepatoma (HepG2) | 0 | 8% | 18% | 6% | 10% |
| Monkey kidney fibroblast (CV1) | 0 | 14% | 28% | 10% | 25% |

Example 7

Pharmacological Test: Erythropoietin Bioactivity

Erythropoietin (EPO) is the main regulator of human erythropoiesis. The molecular mass of EPO is 30-34 kDa.

Recombinant EPO is produced commercially by the expression of EPO cDNA clones in eukaryotic cell lines of Chinese hamster ovary.

Early determination of the potency of rhEPO was carried out in normal rats and mice by following the increase in several parameters such as hematocrit, red blood cell volume and reticulocyte number. Recent investigation estimates that the number of reticulocytes in the circulation is an early indicator of the functional status of erythropoiesis, and estimation of the percentage of reticulocytes in peripheral blood has been used for the assessment of EPO bioactivity.

Products

EPREX, produced by JANSSEN-CILAG Laboratory 2 000 UI/ml

Batch A: EPO 50 UI/kg: a single dose subcutaneously.
Batch B: EPO 100 UI/kg: a single dose subcutaneously
Batch C: EPO 50 UI/kg: a single dose by rectal route (example 4)
Batch D: EPO 100 UI/kg: a single dose by rectal route (example 5)

Protocol

Eight week-old normocythemic mice received a single administration of product, followed by blood sampling 96 h later. Experiments are carried out on 3 rats per batch.

Reticulocyte counting is made by using automated flow cytometry.

Results

| Products | Reticulocytes (%) | Coefficient of Variation (%) |
|---|---|---|
| Batch A: EPO 50 UI/kg SC | 10.69 | 15.79 |
| Batch B: EPO 100 UI/kg SC | 11.24 | 18.51 |
| Batch C: EPO 50 UI/kg RR | 6.19 | 13.67 |
| Batch D: EPO 100 UI/kg RR | 11.93 | 16.70 |

Conclusions

Products C and D (reverse micelles containing erythropoietin) have a significant impact on erythropoiesis, equivalent to EPO administrated subcutaneously.

Example 8

In Vivo Assay: Diabetic STZ Rats Models—Long Acting Insulin

The used product is the one prepared according to example 1.

Purpose of the study: Compare hypoglycemic activity of long acting insulin when administered subcutaneously with the same dosage of insulin incorporated in the reverse micelles according to the invention administrated by the rectal route.

Comments on the Routes of Administration:

Products containing lipidic nanoparticles are degraded in the stomach and duodenum, in particular by lipases. Administration for a subject is preferably carried out at the mouth site via a mucosal absorption. Since this way of administration is not available for rats, the rectal route which allows a mucosal absorption as efficient as an oral administration has been selected. Absorbed substances via the rectal route do not get through liver as substances orally administered and delivered via the mucosal tissue in the blood flow.

Administration Route:
Batch 2: subcutaneous
Batch 3: rectal
Administered Products:
Batch 2: Umulin zinc 5 UI/kg
Batch 3: NP X: Umulin zinc 5 UI/kg in the micellar vector (example 1)
Administered quantity: 2 ml/kg/day via rectal probe
Method:

Administration of streptozotocine (STZ) to male rats Wistar (weight: 250-300 g), intravenously at dose 50 mg/kg, provides an intermediate diabetes between an insulin dependent and a non-insulin dependent diabetes (type 1 and 2). 3 days after administration, glycemia is between 20 and 30 mmol/l and remains nearly stable for the next 7 days.

Substances are administrated daily for 7 days, and glycemia biological assays are made in collected blood samples at D 0, 72 h, and 7 days from the beginning of the treatment.
Results:

| Batch 1 control | | | | | | |
|---|---|---|---|---|---|---|
| Rats n° | D 0 Weight | D 0 Glycemia | D 3 Weight | D 3 Glycemia | D 7 Weight | D 7 Glycemia |
| 25 | 261 | 24.96 | 234 | 28.13 | 223 | 23.05 |
| 31 | 226 | 28.56 | 194 | 29.21 | 191 | 24.22 |
| 32 | 262 | 11.36 | 259 | 15.31 | 260 | 13.30 |
| 34 | 288 | 19.64 | 208 | 19.83 | 199 | 18.54 |
| 50 | 252 | 22.99 | 250 | 22.39 | 256 | 26.46 |
| 66 | 255 | 18.62 | 242 | 16.69 | 240 | 14.59 |

| Batch 2 (Umulin Zn) | | | | | | |
|---|---|---|---|---|---|---|
| Rats n° | D 0 Weight | D 0 Glycemia | D 3 Weight | D 3 Glycemia | D 7 Weight | D 7 Glycemia |
| 52 | 264 | 25.41 | 301 | 5.99 | 302 | 6.01 |
| 72 | 220 | 28.66 | 201 | 3.97 | 221 | 4.30 |
| 73 | 239 | 28.25 | 221 | 5.28 | 210 | 5.21 |
| 74 | 221 | 28.45 | 210 | 4.48 | 220 | 4.78 |
| 75 | 227 | 29.20 | 215 | 4.51 | 213 | 4.64 |
| 77 | 230 | 30.77 | 221 | 5.06 | 220 | 5.05 |

| Batch 3: NP X (nanoparticles Umulin Zn) | | | | | | |
|---|---|---|---|---|---|---|
| Rats n° | D 0 Weight | D 0 Glycemia | D 3 Weight | D 3 Glycemia | D 7 Weight | D 7 Glycemia |
| 60 | 242 | 22.56 | 230 | 6.09 | 225 | 7.43 |
| 61 | 213 | 27.45 | 200 | 12.78 | 197 | 7.08 |
| 62 | 258 | 21.63 | 241 | 9.36 | 238 | 7.71 |
| 63 | 241 | 19.27 | 231 | 7.85 | 228 | 15.79 |
| 64 | 224 | 26.12 | 215 | 21.41 | 215 | 15.30 |
| 65 | 235 | 14.44 | 219 | 8.68 | 218 | 9.39 |

Conclusions:

Insulin Zn administered subcutaneously (batch 2) at a daily dose 5 UI/Kg sets back glycemia to normal rate.

Product NP X (nanoparticles insulin Zn, batch 3) has a significant impact on glycemia: 72 h after the beginning of the treatment, 4 animals out of 6 have regained a normal glycemia equivalent to insulin administrated subcutaneously. Insulin bioavailability for said animals is similar to insulin bioavailability when administered by injection.

The slight difference of the results for injectable insulin on two animals is due to difficulties usually met for rectal administration into animals. Oral administration into a human allows to avoid such difficulties.

Example 9

In Vivo Assay: Diabetic STZ Rats Models—Fast Acting Insulin

Purpose of the study: Compare hypoglycemic activity and bioavailability of fast acting insulin when administered subcutaneously with the same dosage of insulin incorporated in the reverse micelles according to the invention administered by the rectal route.

Protocol

Diabetes is induced in Wistar male rats (weight 150-200 g) by IV injection of streptozotocin (60 mg/kg). After 4 days, treated rats exhibit an insulin dependant diabetes accompanied, after several days, by an insulin resistance. Experiments are carried out on 3 rats per batch.

Only one administration is made, subcutaneously for the reference product, and rectally for tested micelle (Mc) products.

Insulin dosage is the same for reference products and tested Mc products: 5 UI/kg.

Treatment Groups control group non treated STZ fast acting insulin group (fast acting UMULINE) subcutaneous route fast acting insulin group (fast acting UMULINE) rectal route fast acting insulin group Mc UMULINE by rectal route Mc formulation group without insulin by rectal route Glycemia and insulinemia assays are made at 7 time points: 15 min, 30 min, 60 min, 120 min, 180 min, 360 min and 24 hours.

Results

| | Glycemia (mmol/l) | | | | | | | |
|---|---|---|---|---|---|---|---|---|
| | Time (min) | | | | | | | |
| | 0 | 15 | 30 | 60 | 120 | 180 | 360 | 1440 |
| control | 19.98 | 20.13 | 21.59 | 21.37 | 20.18 | 19.65 | 18.91 | 19.68 |
| Standard deviation | 0.73 | 0.81 | 0.17 | 0.15 | 0.19 | 0.46 | 0.87 | 0.46 |
| Subcutaneous fast UMULINE | 21.76 | 17.57 | 9.25 | 4.82 | 3.59 | 4.44 | 19.22 | 21.91 |
| Standard deviation | 1.22 | 1.19 | 2.33 | 0.94 | 0.72 | 1.41 | 2.37 | 1.02 |
| Mc UMULINE | 21.89 | 20.6 | 17.53 | 13.69 | 10.45 | 9.85 | 20.14 | 20.76 |
| Standard deviation | 0.97 | 1.19 | 1.38 | 1.15 | 1.21 | 1.02 | 2.58 | 1.17 |
| Control STZ | 3.3 | 4 | 3.7 | 4.3 | 4.7 | 4.3 | 5 | 4.3 |
| Standard deviation | 0.3 | 0.6 | 0.3 | 0.7 | 0.9 | 0.3 | 0.6 | 0.3 |
| Subcutaneous fast UMULINE | 4.3 | 12.3 | 52.7 | 67.7 | 84.3 | 79.3 | 11.7 | 4 |
| Standard deviation | 0.7 | 1.5 | 2.8 | 7.4 | 4.4 | 7.5 | 1.5 | 0.6 |
| Rectal Mc UMULINE | 4 | 4.7 | 9 | 16.7 | 29 | 31 | 10.3 | 5 |
| Standard deviation | 0.6 | 0.9 | 1.2 | 1.9 | 5.6 | 2.1 | 1.3 | 1 |

Conclusion

Mc absorption kinetics by rectal route is comparable to the one by subcutaneous route for fast insuline: $T_{max}$=2-3 hours.

Elimination kinetics are comparable.

Relative bioavailability of Mc formulation compared to subcutaneous route is of 55%, based on AUC.

Example 10

Optimization of Incorporated Water Quantity

Protocol

Samples containing the relative quantities of peceol, sitosterol and ethanol given in the above examples were prepared by varying quantity of water in which proteins were solubilized. A dilution scale was made by increasing quantity of water with increment of 0.3%.

Samples were homogenized by stirring at 35° C., as described above.

The impact of the quantity of water on the stability of the reverse-micellar system was determined visually (turbidity) and by small-angle X-ray diffraction.

Results

From 6.9% water in the composition (i.e., W is about 0.175) and more, the microemulsion becomes more and more turbid and two phases are appearing where water amount is increasing. The percent of water is expressed by weight of total water:total weight of the composition.

The invention claimed is:

1. A reverse-micellar system comprising at least one hydrosoluble therapeutically active ingredient, a phytosterol, an acylglycerol and water, and wherein the hydrosoluble active ingredient is a peptide, a polypeptide, a protein or a nucleic acid.

2. The reverse-micellar system according to claim 1, wherein the aqueous core of less aqueous core of the reverse-micelles is less than or equal to 100 nm in diameter.

3. The reverse-micellar system according to claim 1, wherein the weight ratio W=(water)/(acylglycerol) is less than or equal to about 2.5.

4. The reverse-micellar system according to claim 1, wherein the weight ratio phytosterol/acylglycerol ranges from 0.01 to 1.

5. The reverse-micellar system according to claim 1, wherein the weight ratio phytosterol/acylglycerol is more than or equal to 0.1.

6. The reverse-micellar system according to claim 1, wherein the weight ratio W=(water)/(acylglycerol) is less than or equal to about 1.

7. The reverse-micellar system according to claim 1, wherein the acylglycerol is:

wherein:

R$_1$ is an acyl residue of a linear or branched, saturated or unsaturated fatty acid having between 14 and 24 carbon atoms, a hydrogen atom, or a mono-, di- or tri-galactose or glucose;

R$_2$ is an acyl residue of a linear or branched, saturated or unsaturated fatty acid having between 2 and 18 carbon atoms;

R$_3$ is an acyl residue of a linear or branched, saturated or unsaturated fatty acid having between 14 and 24 carbon atoms, or an hydrogen atom; and the hydrosoluble active ingredient is a peptide, a polypeptide, a protein or a nucleic acid.

8. The reverse-micellar system according to claim 7, wherein at least one of R$_1$ and R$_3$, is an acyl residue of oleic acid (C18: 1[cis]-9).

9. The reverse-micellar system according to claim 7, wherein R$_2$ is an oleic acid residue (oleoyl group), one of its positional isomers with respect to the double bond (cis-6,7, 9,11 and 13) or one of its iso-branched isomers.

10. The reverse-micellar system according to claim 7, wherein R$_2$ is an acetyl group.

11. The reverse-micellar system according to claim 7, wherein R$_3$ is a hydrogen atom.

12. The reverse-micellar system according to claim 7, wherein the acylglycerol is 1,2-diolein and 1-oleoyl-2-acetyl glycerol.

13. The reverse-micellar system according to claim 1, wherein the phytosterol is sitosterol.

14. A pharmaceutical composition comprising reverse micelles as defined in claim 1 and a pharmaceutically acceptable support.

15. The reverse-micellar system according to claim 5, wherein the weight ratio phytosterol/acylglycerol is from 0.1 to 0.2.

16. The reverse-micellar system according to claim 8, wherein only one of $R_1$ and $R_3$ is an acyl residue of oleic acid (C18: 1[cis]-9).

17. The reverse-micellar system according to claim 1, wherein the nucleic acid is DNA or RNA or fragments thereof.

18. The reverse-micellar system according to claim 17, wherein the RNA is RNAi.

19. The reverse-micellar system according to claim 7, wherein the peptide, the polypeptide, the protein or the nucleic acid is insulin, erythropoietin, leptin, growth factors, growth hormone releasing hormones, colony stimulating factors, hydrosoluble hormones, luteinising hormone releasing hormone (LHRH) or analogues thereof, interferons, cytokines, DNA, RNA fragments or plasmids, RNA interference, immunogenic agents, and/or vaccine agents.

20. The reverse-micellar system according to claim 19, wherein the hydrosoluble hormones are parathyroid hormone or fractions or analogues thereof.

21. The reverse-micellar system according to claim 19, wherein the luteinising hormone releasing hormone (LHRH) or analogues thereof are nafarelin, buserelin, or goserelin.

22. The reverse-micellar system according to claim 1, wherein the peptide, the polypeptide, the protein or the nucleic acid is insulin, erythropoietin, leptin, growth factors, growth hormone releasing hormones, colony stimulating factors, hydrosoluble hormones, luteinising hormone releasing hormone (LHRH) or analogues thereof, interferons, cytokines, DNA, RNA fragments or plasmids, RNA interference, immunogenic agents, and/or vaccine agents.

23. The reverse-micellar system according to claim 22, wherein the hydrosoluble hormones are parathyroid hormone or fractions or analogues thereof.

24. The reverse-micellar system according to claim 22, wherein the luteinising hormone releasing hormone (LHRH) or analogues thereof are nafarelin, buserelin, or goserelin.

* * * * *

UNITED STATES PATENT AND TRADEMARK OFFICE
CERTIFICATE OF CORRECTION

PATENT NO.         : 8,637,314 B2                                                            Page 1 of 1
APPLICATION NO.  : 11/718513
DATED              : January 28, 2014
INVENTOR(S)        : Jean-Claude Maurel It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1641 days.

Signed and Sealed this
Twenty-second Day of September, 2015

Michelle K. Lee
*Director of the United States Patent and Trademark Office*